United States Patent [19]
Frechette et al.

[11] Patent Number: 5,865,767
[45] Date of Patent: Feb. 2, 1999

[54] GUIDEWIRE HAVING COMPOUND TAPER

[75] Inventors: Robert Frechette, Fort Lauderdale, Fla.; Bill Dorcas, West Columbia, S.C.; Brian Gore, Fort Lauderdale, Fla.

[73] Assignee: Cordis Corporation, Miami Lakes, Fla.

[21] Appl. No.: 677,887

[22] Filed: Jul. 10, 1996

[51] Int. Cl.⁶ .................................................. A61B 5/00
[52] U.S. Cl. ............................................................ 600/585
[58] Field of Search .................... 600/433–436, 600/585

[56] References Cited

U.S. PATENT DOCUMENTS

| | | | |
|---|---|---|---|
| 4,554,929 | 11/1985 | Samson et al. | 128/772 |
| 4,721,117 | 1/1988 | Mar et al. | 600/585 |
| 5,120,308 | 6/1992 | Hess | 604/95 |
| 5,174,302 | 12/1992 | Palmer | 128/772 |
| 5,259,393 | 11/1993 | Corso, Jr. et al. | 128/772 |
| 5,267,573 | 12/1993 | Evans et al. | 128/772 |
| 5,402,799 | 4/1995 | Colon et al. | 600/585 |
| 5,417,665 | 5/1995 | DeLa Mata et al. | 604/164 |
| 5,443,907 | 8/1995 | Slaikeu et al. | 600/585 |
| 5,520,194 | 5/1996 | Miyata et al. | 600/585 |

*Primary Examiner*—Max Hindenburg
*Attorney, Agent, or Firm*—Watts, Hoffmann, Fisher & Heinke, Co., LPA

[57] ABSTRACT

A guidewire for a catheter having a corewire that includes a compound taper at its distal end portion. The compound taper of the corewire has a first taper that transitions into a second taper. The first taper proximal of the distal tip of the corewire has a greater angle with respect to the central longitudinal axis of the corewire, and is shorter in length than the second taper.

4 Claims, 1 Drawing Sheet

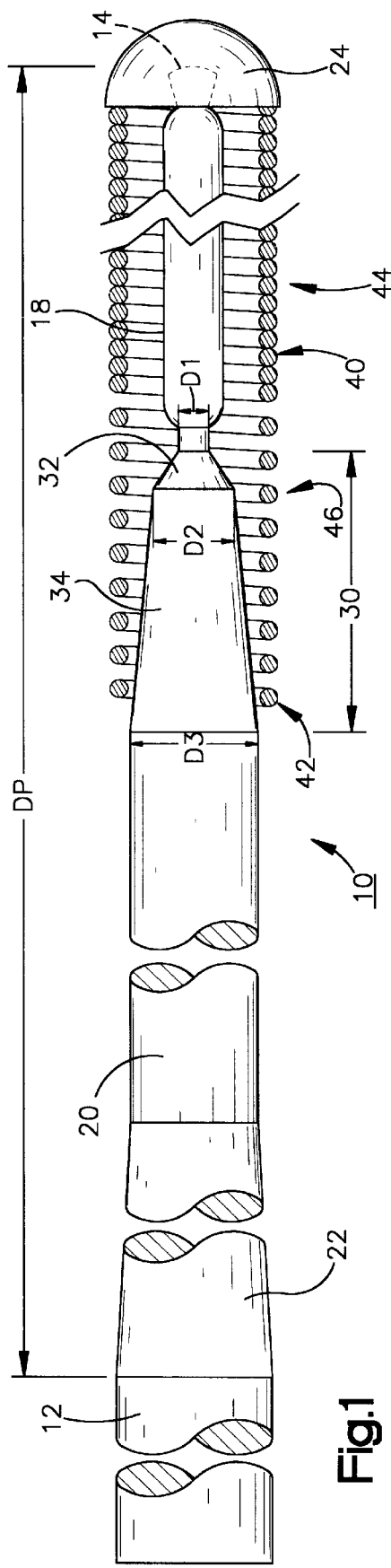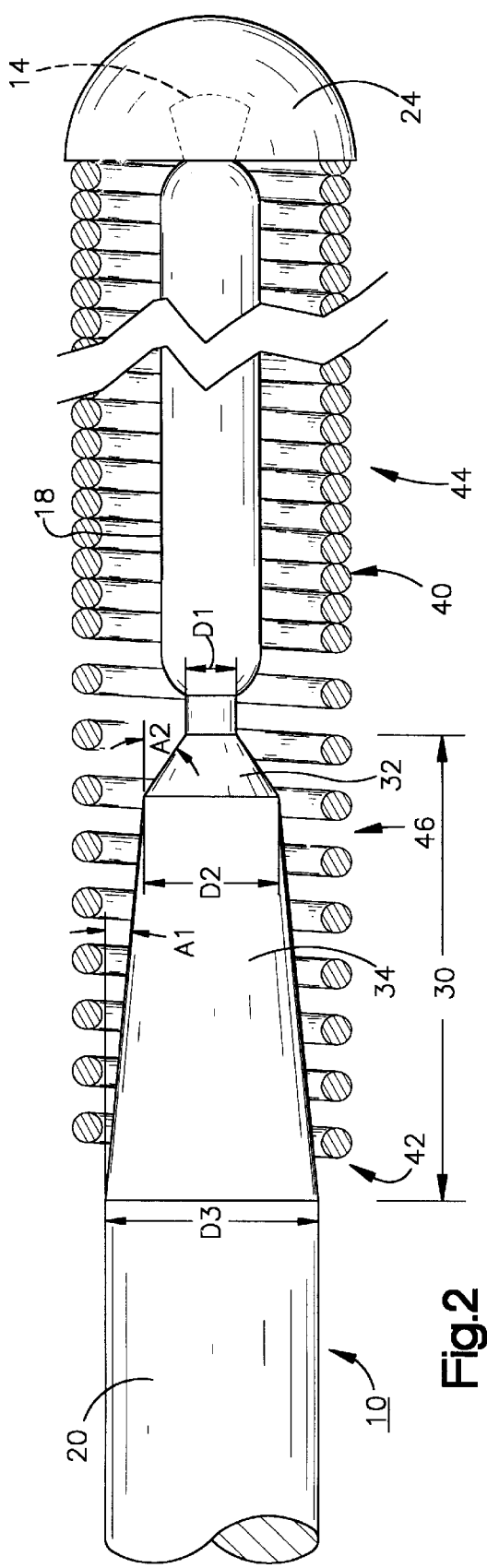

GUIDEWIRE HAVING COMPOUND TAPER

BACKGROUND OF THE INVENTION

Guidewires are used to assist the insertion of diagnostic and therapeutic catheters into body passages such as arteries and vessels. To guide the catheter to the appropriate location the guidewire is inserted into the patient and advanced through the cardiovascular system while the progress of the guidewire is monitored on an x-ray imaging screen. In some procedures, the guidewire must be advanced and steered through extremely tortuous cardiovascular passageways in order to reach the area to be treated or diagnosed. Accordingly, it is important that the distal tip of the guidewire is flexible to facilitate the advancement and navigation of the guidewire along its tortuous journey. Likewise, a flexible tip is also needed to avoid damaging inner walls of the vessels and arteries with which the tip comes in contact as it is advanced. It has therefore been the subject of much inventive activity to develop guidewires and guidewire tips that are extremely flexible and steerable, so that the guidewire can be easily manipulated into various branches and passages in the vessels and arteries.

Not all catheterization procedures require that the guidewire and catheter be advanced through extremely tortuous pathways. In more routine cases, the physician need only guide the catheter to treat or diagnose regions in primary or otherwise more accessible passage ways of the cardiovascular system. Thus, in more routine cases, it is not necessary to navigate the guidewire through a tortuous pathway. In such cases, the advancements made in extreme flexibility of guidewires and guidewire tips can actually hinder the progress of the physician because, during advancement, the guidewire tends to find and follow side branches and undesired passageways. This increases that amount of work required by the physician and unnecessarily prolongs the duration of an otherwise routine procedure.

There is a need for guidewires for use in routine catheterization procedures that will be less likely to find unwanted side branches and more likely to travel in a generally forward direction. Nevertheless, flexibility is still quite important in any catheterization procedure, both for avoiding trauma to vessel or artery walls and for maintaining steerability. Accordingly, there is a need to provide an easily manufacturable guidewire that has the desired ability to avoid unnecessary detours without sacrificing the flexibility and steerability required of a guidewire.

DISCLOSURE OF THE INVENTION

The present invention provides a guidewire having a corewire that includes a compound taper at its distal end portion. The compound taper provides an abrupt change in stiffness from an extremely flexible distal tip portion, to a stiffer but still quite flexible proximal portion of the guidewire. Due to the abrupt change in stiffness the guidewire will tend to proceed in a generally forward or straight direction rather than follow the extremely flexible tip portion into side branches. By contrast, a single longer taper will tend to follow the flexible tip portion into side branches, requiring the physician to at least partially withdraw the guidewire and try again.

The compound taper includes a first, relatively steep taper portion and a second, more gradual taper portion. The first taper portion of the compound taper provides the abrupt change in stiffness and imparts a rather significant stress concentration over a relatively short distance of the corewire. The sudden increase in stiffness, coupled with the concentration of stress at this narrow region of the corewire provides increased control over the distal portion of the guidewire, making it easier to prevent it from following the flexible tip into side passages. The second more gradual taper portion of the compound taper eases the stiffness transition, and distributes the concentration of stress proximally from the first taper to reduce the possibility of kinking or breakage at the stress point associated with the first taper.

Advantageously, the abrupt stiffness transition, followed by the more gradual transition of the compound taper of the invention, provides a sufficient amount of control to generally keep the guidewire from inadvertently proceeding down side branches, while maintaining sufficient flexibility to minimize trauma to the vessel and artery walls. This allows a physician faced with a more routine procedure in which a stent or balloon need only be positioned in a main passage, to select a guidewire according to the invention and carry out the procedure with less work and in less time. In addition, since the compound taper is simply a novel aspect of the corewire profile, it is easily manufactured according to known techniques for grinding corewires, and does not require the assembly of different materials such as reinforcing tubes, solders or brazes.

It is therefore one aspect of the invention to provided an elongate flexible guidewire comprising a core wire, said core wire comprising a distal portion including a distal tip and a compound taper portion proximal of said distal tip. The compound taper portion comprises a first taper portion from a first diameter of the corewire to a second diameter of the corewire that is greater than said first diameter, and a second taper portion from said second diameter of the corewire to a third diameter of the core wire that is greater than said second diameter. The compound taper portion continuously tapers from said first diameter to said third diameter and the first taper portion has an angle with respect to the central longitudinal axis of the guidewire that is greater than the angle of the second taper portion with respect to the central longitudinal axis.

In a preferred embodiment, the first taper portion has an angle with respect to the central longitudinal axis that is from about 30° to about 50°, and the second taper portion has an angle with respect to the central longitudinal axis that is from about 10° to about 20°. Still more preferably, the first taper portion is from about 0.20 inches to about 0.50 inches in length, and the second taper portion is from about 0.75 inches to about 1.75 inches in length.

Many additional features, advantages and a fuller understanding of the invention will be had from the following detailed description of the preferred embodiments and accompanying drawings.

BRIEF DESCRIPTION OF THE DRAWINGS

FIG. 1 is an elevation segmented view of a flexible guidewire constructed in accordance with the invention.

FIG. 2 is an elevation of a compound taper portion of a flexible guidewire according to the invention.

DETAILED DESCRIPTION OF THE PREFERRED EMBODIMENTS

Referring to FIG. 1, a guidewire according to the invention is shown including an elongate corewire 10, preferably formed from stainless steel or the like. The corewire 10 is constructed to include a first proximal uniform diameter portion 12, which extends the majority of the length of the core wire 10. From the proximal uniform diameter portion 12, the corewire includes a distal portion, designated in FIG. 1 as the portion DP, that extends to its extreme distal tip 14. Along the distal portion DP of the corewire between proximal uniform diameter portion 12 and distal tip 14, the corewire 10 reduces in diameter. Working backward from the distal tip 14 to the proximal uniform diameter portion 12, the preferred corewire includes an extremely flexible, generally flat ribbon portion 18. The ribbon portion 18 transitions into a compound taper portion 30, which includes a first compound taper portion 32, and a second compound taper portion 34. In the preferred embodiment the compound taper portion 30 transitions into a second proximal uniform diameter portion 20. The second proximal uniform diameter portion 20 then transitions into a third taper portion 22 which tapers to an increased diameter terminating in the first proximal uniform diameter portion 12.

Typical guidewires have lengths ranging from length of about 70 to 120 inches, with the proximal uniform diameter portion 12 typically comprising all but the distal most 12–15 inches of the corewire. The proximal uniform diameter portion 12 of most guidewires will have diameters on the order of from about 0.010 to 0.038 inches. Of course, the dimensions of proximal portion 12 can vary in the industry depending on the materials used, and procedures for which the guidewire is intended as would be apparent to those of ordinary skill in the art. Preferably, the first proximal uniform diameter portion 12 is coated on its outer surface with a lubricous coating (not shown), such as polytetrafluoroethylene (PTFE) or the like to reduce friction and facilitate its movement within a catheter lumen as is known in the art.

The most important aspect of the invention is the compound taper portion 30 of the corewire. The first taper portion 32 of the compound taper 30 creates a narrow stress concentration in the corewire and imparts an abrupt change in stiffness from the flexible ribbon portion 18. The stress concentration abruptly increases the force necessary to bend the guidewire at the short taper portion 32. As a result, when the flexible ribbon portion 18 begins to bend down a side branch as the guidewire is advanced, the stress concentration at portion 32 resists the tendency to bend and follow the tip. When additional forward force is applied to the guidewire, the flexible tip pulls or snaps out of the side branch and proceeds in a forward direction.

The concentration of stress forces at the first taper portion 32 can cause the guidewire to kink or the corewire to break at the transition from the flexible tip to the compound taper. Accordingly, the first taper portion 32 transitions directly into the more gradual second taper portion 34. The second taper portion 34 smooths out the stiffness transition and distributes the stress proximally along the corewire 10 when the corewire is bent. By ensuring that the first taper portion 32 is short and transitions directly into the longer, more gradual second taper portion 34, the bending stresses are sufficiently distributed so as to prevent kinking or breakage of the corewire at the first taper portion 32.

Preferably, the first taper portion 32 increases the stiffness of the corewire by about 35% to about 55%, with an increase in stiffness of about 50% being especially preferred in this area of the compound taper. This provides the large, instantaneous stiffness change from the flexible ribbon tip that prevents the core wire from tending to follow the flexible tip into unintended side passages and the like. By smoothing the transition and distributing the stress along the second compound taper portion 34, the overall flexibility and steerability of the guidewire, as well as its structural integrity, is not adversely effected.

As can be seen in FIGS. 1 and 2, the first taper portion 32 of the compound taper 30 is an abrupt taper that transitions from a first diameter of the corewire D1 to a second diameter of the core wire D2. In a typical case, the first diameter D1 can range from about 0.0025 to 0.0035 inches. The second diameter D2 will be on the order of about 0.005 inches, but will vary depending on the length of the first taper portion 32. The second taper portion 34 of the compound taper portion 30 is more gradual and extends from the second diameter of the corewire D2 to a third diameter of the corewire D3, which will typically be on the order of from about 0.0070 to 0.0090 inches. Importantly, the first taper portion 32 is shorter than the second taper portion 34. Preferably, the first taper portion will range from about 0.200 to 0.500 inches in length, and the second taper portion 34 will range from 0.75 to 1.75 inches in length. Moreover, the first taper portion 32 makes an angle A1 with respect to the central longitudinal axis of the corewire of from about 30° to about 50°, and still more preferably about 50°. The second taper portion 34 preferably makes an angle A2 with respect to the central longitudinal axis of the corewire of from about 10° to about 20°, and more preferably about 20°.

As noted, the compound taper portion 30 is interposed between the flexible tip portion 18 and a second proximal uniform diameter portion 20. The second proximal uniform diameter portion will generally constitute about 80 to 90% of the distal most 12 to 15 inches of the guidewire comprising the distal portion DP. The portion 20 of the corewire, which has a uniform diameter corresponding to diameter D2, serves as a staging area or platform for manipulating devices associated with the catheter. In practice, the second uniform diameter portion 20 will be located across a lesion, stenosis, occlusion or the like. Subsequently, a catheter is moved over the guidewire such that a stent, balloon, a balloon carrying a stent or the like is positioned on the portion 20. Thus, when the stent is deployed or the balloon inflated, the portion 20 serves to support the procedure. Accordingly, the dimensions associated with the second proximal uniform diameter portion 20 may vary depending upon the procedure and catheter with which the guidewire is to be used. Moreover, while the second uniform diameter portion 20 will be present in most guidewires associated with the invention, it is contemplated that the compound taper of the invention will be useful in any guidewire where the control associated with the compound taper is desired.

As with the first proximal uniform diameter portion 12, the second proximal uniform diameter portion 20 may be coated with a lubricous material such as PTFE. In addition, it is frequently advantageous to coat or plate portion 20, such as by electroplating, with a radiopaque material such as silver, gold, platinum, tantalum or the like (not shown). This serves to assist the physician in locating the portion 20 across, for example, an occlusion and thereafter locating a balloon or stent at the appropriate place along the guidewire. As seen in FIG. 1, the second proximal uniform diameter portion 20 transitions into the first proximal uniform diameter portion 12 through a third taper portion 22, which is also coated with PTFE and/or a radiopaque material. Typically, the third taper portion will be on the order of about 1.2 inches in length.

The ribbon portion 18 is a constant diameter portion of the corewire about 0.60 to about 1.0 inches in length that has been pressed flat to enhance flexibility and steerability. Prior to flattening, the corewire typically has a diameter of 0.0025 to 0.0035 through portion 18. The ribbon portion 18 commences about 0.20 inches distal of the first taper portion 3.2 of the compound taper 30 and terminates about 0.20 to 0.40 inches proximal of the extreme distal tip 14 of the corewire. This latter portion of corewire provides structure on which to weld the coil 40 to the corewire 10. In some instances, a physician will prefer a slightly stiffer tip. In this case, ribbon portion 18 is not flattened and the corewire extends all the way to its distal tip 14 at a constant diameter on the order of 0.0025 to 0.0035, or increases in diameter at the distal most 0.20 to 0.40 inches to provide structure for the weld.

Surrounding the core wire between the distal tip 14 and the second proximal uniform diameter portion 20 is a flexible spring or coil 40. The coil 40 is secured to the core wire distal end 14 by a weld 24 or other means of attachment such as brazing, adhesive or the like. Preferably, the weld or braze 24 defines a smooth hemispherical bead which does not damage the inner lining of blood vessels, arteries or the like with which the guidewire tip comes in contact. The proximal end 42 of coil 40 is secured to the core wire 10 by soldering, brazing adhesive or the like, preferably at a middle portion of the second taper portion 34 of the compound taper 30. The purpose of the coil 40 is to increase flexibility of the distal tip portion of the guidewire, and to provide radiopacity. As shown, the coil 40 includes a first portion 44, comprising the distal most 0.5 to 1.0 inches of the coil, wherein the coils are tightly packed with a gap on the order of 0.001 to 0.002 inches, and a second portion 46, roughly comprising the proximal 0.20 inches of coil 40, wherein the coils are slightly spaced apart a distance of about 0.005 to 0.010 inches to facilitate securement to the corewire 10. The overall length of coil 40 is about 0.7 to about 1.2 inches. However, there are numerous coil configurations known in the art suitable for use in connection with a core wire having a compound taper according to the invention. Examples of various coil configurations include those disclosed in U.S. Pat. Nos. 5,259,393 and 5,174,302, incorporated herein by reference.

Guidewires as disclosed herein can be easily manufactured using known techniques of corewire grinding as would be apparent to those of ordinary skill in the art. Given the parameters disclosed herein, one skilled in the art need only input the inventive corewire profile into a computer and the corewire will be ground to the desired dimensions.

Many modifications and variations of the invention will be apparent to those skilled in the art in light of the forgoing detailed disclosure. Therefore, within the scope of the appended claims, the invention can be practiced otherwise than as specifically shown and described.

What is claimed is:

1. An elongate flexible guidewire comprising a core wire, said core wire comprising a distal portion including a distal tip, said distal portion including a compound taper portion proximal of said distal tip, said compound taper portion comprising a first taper portion extending from a first diameter of said core wire to a second diameter of said core wire that is greater than said first diameter, and a second taper portion adjacent the first taper portion and extending from said second diameter of said core wire to a third diameter of said core wire that is greater than said second diameter, said compound taper portion continuously tapering from said first diameter to said third diameter, an outer surface of said first taper portion having an angle with respect to a central longitudinal axis of said guidewire that is greater than an angle of an outer surface of said second taper portion with respect to said central longitudinal axis.

2. The guidewire according to claim 1 wherein said angle of the outer surface of the first taper portion is from about 30° to about 50°, and said angle of the outer surface of the second taper portion is from about 10° to about 20°.

3. The guidewire according to claim 1 wherein said first taper portion is shorter in length along the central longitudinal axis than said second taper portion.

4. The guidewire according to claim 1 wherein said first taper portion is from about 0.20 inches to about 0.50 inches in length along the central longitudinal axis, and said second taper portion is from about 0.75 inches to about 1.75 inches in length along the central longitudinal axis.

* * * * *